(12) United States Patent
Hegazi et al.

(10) Patent No.: US 10,845,306 B2
(45) Date of Patent: *Nov. 24, 2020

(54) DETERMINING COMPOSITION OF A SAMPLE

(71) Applicant: Saudi Arabian Oil Company, Dhahran (SA)

(72) Inventors: Ezzat Hegazi, Windsor (CA); Vincent Cunningham, Ferbane (IE)

(73) Assignee: Saudi Arabian Oil Company, Dhahran (SA)

( * ) Notice: Subject to any disclaimer, the term of this patent is extended or adjusted under 35 U.S.C. 154(b) by 209 days.

This patent is subject to a terminal disclaimer.

(21) Appl. No.: 15/681,940

(22) Filed: Aug. 21, 2017

(65) Prior Publication Data
US 2019/0056325 A1 Feb. 21, 2019

(51) Int. Cl.
*G01N 21/64* (2006.01)
*G01N 33/22* (2006.01)
(Continued)

(52) U.S. Cl.
CPC ....... *G01N 21/6428* (2013.01); *G01N 21/645* (2013.01); *G01N 21/33* (2013.01);
(Continued)

(58) Field of Classification Search
CPC ............. G01N 21/6428; G01N 21/645; G01N 21/6456; G01N 21/33; G01N 33/28;
(Continued)

(56) References Cited

U.S. PATENT DOCUMENTS

| 4,771,629 A * | 9/1988 | Carlson ..................... G01J 3/42 |
| | | 73/23.35 |
| 5,578,833 A | 11/1996 | Ohmi et al. |

(Continued)

FOREIGN PATENT DOCUMENTS

| EP | 2275801 | 1/2011 |
| IN | 200561 | 2/2007 |

(Continued)

OTHER PUBLICATIONS

Patra et al., "Effect of sample geometry on synchronous fluorimetric analysis of petrol, diesel, kerosene and their mixtures at higher concentration," Analyst, Jun. 2000, vol. 125, No. 8; pp. 1383-1386.

(Continued)

*Primary Examiner* — Michael L Hobbs
(74) *Attorney, Agent, or Firm* — Fish & Richardson P.C.

(57) ABSTRACT

A single-wavelength light source is configured to generate an excitation light source. A sample holder that defines an inner cavity is capable of holding a sample and includes a surface transparent to the excitation light source. One or more mounts are attached to at least one of the light source or the sample holder. The mounts are configured to change an incident angle of the excitation light source on the surface. One or more optical components are positioned in a path of a fluorescence emission emitted from the surface and guide the fluorescence emission to a detector. A detector detects an intensity of the fluorescence emission.

9 Claims, 9 Drawing Sheets

(51) Int. Cl.
    *G01N 33/28*     (2006.01)
    *G01N 21/13*     (2006.01)
    *G01N 21/39*     (2006.01)
    *G01N 21/33*     (2006.01)

(52) U.S. Cl.
    CPC ....... *G01N 21/6456* (2013.01); *G01N 33/225* (2013.01); *G01N 33/28* (2013.01); *G01N 2021/135* (2013.01); *G01N 2021/392* (2013.01); *G01N 2021/6482* (2013.01); *G01N 2021/6484* (2013.01); *G01N 2201/129* (2013.01)

(58) Field of Classification Search
    CPC ... G01N 2021/6482; G01N 2021/6484; G01N 2021/135; G01N 2021/392; G01N 2201/129; C12M 23/22; C12M 29/10; C12M 29/26; C12M 41/00; C12M 35/04; B01L 3/5027
    See application file for complete search history.

(56) References Cited

U.S. PATENT DOCUMENTS

| | | | |
|---|---|---|---|
| 7,202,947 B2 | 4/2007 | Liu et al. | |
| 8,980,179 B2 | 3/2015 | Geddes | |
| 9,081,175 B2 | 7/2015 | Yang | |
| 2003/0099422 A1 | 5/2003 | Beom et al. | |
| 2003/0205681 A1* | 11/2003 | Modlin | G01N 21/6428 |
| | | | 250/458.1 |
| 2007/0237679 A1 | 10/2007 | Hegazi | |
| 2016/0356717 A1* | 12/2016 | Fujii | G01N 21/648 |
| 2017/0131204 A1* | 5/2017 | Sieben | G01N 21/553 |
| 2017/0205387 A1 | 7/2017 | Hegazi et al. | |
| 2018/0017493 A1 | 1/2018 | Nakamura et al. | |

FOREIGN PATENT DOCUMENTS

| | | |
|---|---|---|
| UA | 89533 | 4/2014 |
| WO | 2010010751 | 1/2010 |
| WO | 2016098581 | 6/2016 |

OTHER PUBLICATIONS

International Search Report and Written Opinion issued in International Application No. PCT/US2018/047207 dated Nov. 7, 2018, 7 pages.
International Search Report and Written Opinion issued in International Application No. PCT/US2018/047217 dated Nov. 8, 2018, 7 pages.
Gulf Cooperation Council Examination Report issued in GCC Application No. GC 2018-35888 dated Mar. 24, 2020, 5 pages.

* cited by examiner

DETERMINING COMPOSITION OF A SAMPLE

TECHNICAL FIELD

This disclosure relates to fluid fluorescence.

BACKGROUND

Some fluids can fluoresce, that is, they give off light when stimulated by a certain wavelength of light from an external source. Different fluids are sensitive to different wavelengths of light and different fluids fluoresce different wavelengths of light when stimulated or excited.

SUMMARY

This disclosure relates to determining a composition of a sample.

An example implementation of the subject matter described within this disclosure is a fluorescence-measurement apparatus with the following features. A single-wavelength light source is configured to generate an excitation light source. A sample holder that defines an inner cavity is capable of holding a sample and includes a surface transparent to the excitation light source. One or more mounts are attached to at least one of the light source or the sample holder. The mounts are configured to change an incident angle of the excitation light source on the surface. One or more optical components are positioned in a path of a fluorescence emission emitted from the surface and guide the fluorescence emission to a detector. A detector detects an intensity of the fluorescence emission.

Aspects of the example implementation, which can be combined with the example implementation alone or in combination, include the following. The one or more mounts includes a rotatable mount attached to a base of the sample holder and can rotate the surface of the sample holder in relation to the excitation light source.

Aspects of the example implementation, which can be combined with the example implementation alone or in combination, include the following. An axis of rotation of the sample holder is positioned vertically through the center of the sample holder.

Aspects of the example implementation, which can be combined with the example implementation alone or in combination, include the following. An axis of rotation of the sample holder is positioned vertically through the center of the surface of the sample holder.

Aspects of the example implementation, which can be combined with the example implementation alone or in combination, include the following. The surface is tilted relative to a vertical axis in range from 0°-80°.

Aspects of the example implementation, which can be combined with the example implementation alone or in combination, include the following. The light source includes a laser in an ultraviolet spectrum at a defined wavelength.

Aspects of the example implementation, which can be combined with the example implementation alone or in combination, include the following. The detector includes a monochromator coupled to a photomultiplier.

Aspects of the example implementation, which can be combined with the example implementation alone or in combination, include the following. A filter is positioned between the surface and the detector and is configured to pass a specified range of wavelengths and filter out wavelengths different from the specified range.

Aspects of the example implementation, which can be combined with the example implementation alone or in combination, include the following. The one or more optical components can include a lens positioned between the surface and the detector that is configured to focus the fluorescence emission on an inlet of a fiber optic cable. A fiber optic cable can be positioned between the lens and the detector with the inlet configured to receive the focused fluorescence emission and an outlet positioned to direct the focused fluorescence emission to the detector.

Aspects of the example implementation, which can be combined with the example implementation alone or in combination, include the following. The sample can include a hydrocarbon fluid.

An example of the subject matter described within this disclosure is a method with the following features. A fluid sample is received by a sample holder defining an inner cavity capable of holding a sample and that includes a surface that is transparent to an excitation light source. Fluorescence is induced in the fluid sample by a light produced by a single-wavelength light source. An angle of incidence between the surface of the sample holder and the light is changed. A change in fluorescence intensity is detected by a detector as the angle of incidence is changed.

Aspects of the example method, which can be combined with the example implementation alone or in combination, include the following. A plot of fluorescence intensity vs. the angle of incidence is plotted. The plot is compared to a library of plots. A content of the fluid sample is determined in response to comparing the plot.

Aspects of the example method, which can be combined with the example implementation alone or in combination, include the following. Changing the angle of incidence includes rotating the sample holder.

Aspects of the example method, which can be combined with the example implementation alone or in combination, include the following. Rotating the sample holder can include rotating the sample holder about an axis of rotation of the sample holder that is positioned vertically through the center of the sample holder.

Aspects of the example method, which can be combined with the example implementation alone or in combination, include the following. Rotating the sample holder can include rotating the sample holder about an axis of rotation of the sample holder that is positioned vertically through the center of a face of the sample holder.

Aspects of the example method, which can be combined with the example implementation alone or in combination, include the following. Changing an angle of incidence is controlled by a microprocessor.

Aspects of the example method, which can be combined with the example implementation alone or in combination, include the following. The fluid sample includes hydrocarbon fluid.

Aspects of the example method, which can be combined with the example implementation alone or in combination, include the following. Changing the angle of incidence includes varying the angle between 0°-80°.

An example implementation of the subject matter described within this disclosure is a fluid identification system with the following features. A sample holder is filled with an unknown fluid. The sample holder is transparent to a specified wavelength of light. A laser is capable of directing a laser beam towards a face of the sample holder. A detector is directed towards the face of the sample holder.

The detector is capable of detecting florescent emissions from the unknown fluid within the sample holder. a microprocessor is also included. A computer-readable storage medium stores instructions that are executable by the microprocessor. The instructions include emitting a laser beam from a laser at the face of the sample holder, inducing fluorescence in the fluid by the laser beam produced by a laser at a specified wavelength, changing an angle of incidence between the face of the sample holder and the laser beam, detecting a change in fluorescence intensity as the angle of incidence is changed, plotting a plot of fluorescence intensity vs. the angle of incidence, comparing the plot to a library of plots, and determining a composition of the fluid in response to comparing the plot.

Aspects of the example system, which can be combines with the example implementation alone or in combination, include the following. The unknown fluid includes a hydrocarbon fluid.

Aspects of the example system, which can be combines with the example implementation alone or in combination, include the following. Rotating the sample holder includes rotating the sample holder about an axis of rotation of the sample holder that is positioned vertically through the center of the sample holder.

Aspects of the example system, which can be combines with the example implementation alone or in combination, include the following. Rotating the sample holder comprises rotating the sample holder about an axis of rotation of the sample holder that is positioned vertically through the center of a surface of the sample holder.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

At remote work sites and facilities, such as an off-shore production or drilling platform, technicians can be asked to identify unknown substances. The reasons for identification can include checking for contamination, verifying a mixture ratio, determining a substance in an unlabeled container, or other reasons. Many identification tests of sample are typically sent off-site to a lab and can have a turn-around time of several days or longer. In many instances, it is preferable for an on-site technician to be able to identify the substance quickly and on-site.

This disclosure describes a method and apparatus for identifying fluids based on fluorescence of the fluids. The apparatus can include an excitation light source for inducing fluorescence in a sample, a sample holder for holding the sample, and a photodetector to measure the intensity of the fluorescence. The excitation light beam can be directed at the sample at a non-perpendicular angle to a flat, transparent surface of the sample holder. The laser can induce an inner-filter effect in the fluid due to a depth of penetration of the laser beam into the fluid. The detector detects the fluorescence intensity of the inner-filter effect is detected and the detector can be configured to detect the wavelength of the expected fluorescence. A beam dump may capture the light reflected off of the face of the sample holder to prevent or otherwise reduce interference with the detected fluorescence. In some implementations, the sample holder is rotated in order to vary a depth of penetration of the light beam into the fluid, and consequently the fluorescent intensity of the inner-filter effect can vary. In some implementations, the sample holder is held stationary and the laser is moved to different positions to vary a depth of penetration of the laser beam into the sample (such as fluid), and consequently the fluorescent intensity of the inner-filter effect can vary. The intensity variations are recorded against the angle of incidence between the laser and the front of the sample holder. The plot produced from this test can be used to identify the fluid.

Figure 1:
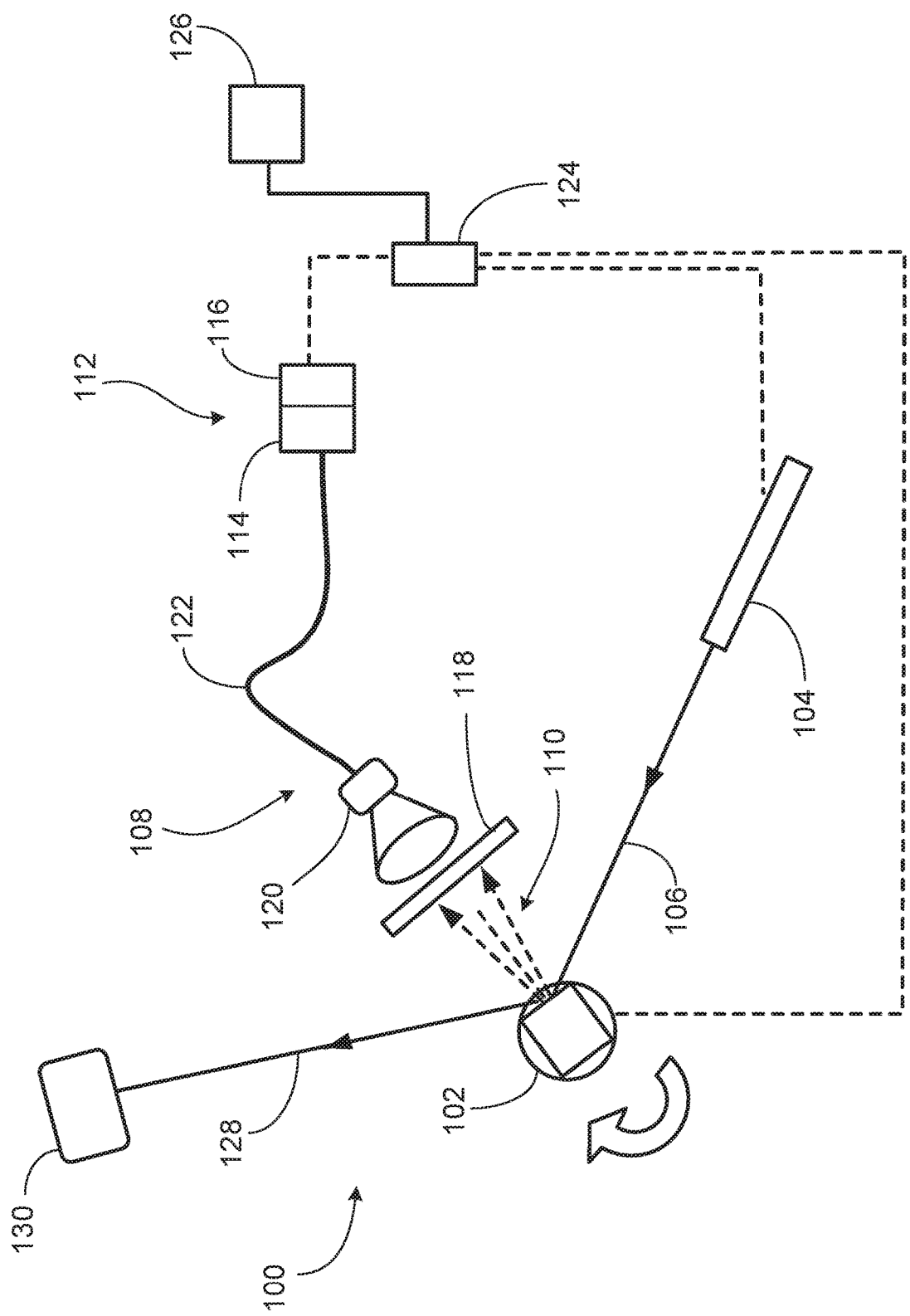
FIG. 1 is a schematic diagram of an example fluorescence-measurement apparatus.

FIG. 1 shows a fluorescence-measurement apparatus 100 in accordance with some implementations of the present disclosure. For example, the fluorescence-measurement apparatus 100 can be configured to measure variations in fluorescent intensities based on incident angles of an excitation light. At a high level, the apparatus 100 includes a sample holder 102, an excitation light source 104 configured to direct excitation light on the sample hold 102, and a detector 112 configured to detect fluorescent intensity in response to the excitation light. By plotting the fluorescent intensity as a function of incident angle, the apparatus 100 can, in some implementations, identify a sample contained in the sample holder 102.

The sample holder 102 that defines an inner cavity capable of holding a sample, such as a fluid. The sample holder 102 includes a surface that is transparent to an excitation light source 104. The sample holder 102 can be a quartz cuvette, a glass sample container, or any other sample container with a flat surface that is transparent to the specified wavelengths of the light source 104. In some implementations, only a single side of the sample holder is transparent to the specified wavelengths of the light source 104.

The excitation light source 104 emits a beam 106 of a single wavelength of light that is capable of generating fluorescence in a sample. In some implementations, the excitation light source 104 emits a beam 106 of light containing multiple wavelengths with at least one wavelength that is capable of generating fluorescence in the sample. In some implementations, the light source 104 can be a laser that emits a laser beam at a defined wavelength, for example, in an ultraviolet wavelength. In some implementations, the wavelength of the light beam 106 can be between 266 nanometers and 355 nanometers. The light source can have a power output between twenty and fifty milliwatts. In some implementations, the sample can fluoresce after one second of exposure to the light beam 106. The light source can emit either a continuous or pulsed light beam.

In order to change the incident angle of the excitation light, the apparatus 100 can also include one or more mounts attached to either the light source 104, the sample holder 102, or both. The mounts can be configured to change an incident angle of the beam 106 relative to the surface of the sample holder 102. For example, the mount can move the light source 104 in a circular path around the sample holder 102. In some implementations, the incident angle can range from 0°-80°. The angle of incidence can be changed continuously or in steps. For example, 5° steps can be taken between measurements.

The apparatus 100 can also include one or more optical components 108 positioned between the sample holder 102 and the detector 112. For example, the one or more optical components are position in a path of fluorescence emission 110 emitted from the surface of the sample holder 102. In the instances, the one or more optical components 108 are configured guide or otherwise pass the fluorescence emission 110 to the detector 112. As illustrated, the one or more optical components 108 includes a filter 118 positioned between the surface of the sample holder 102 and the detector 112. The filter 118 can pass a specified range of wavelengths and filter out or otherwise block wavelengths different from the specified range. The filter 118 can be a notch filter or any other optical filter. The optical components 108 can also include a lens 120 positioned between the filter 118 and a fiber optic cable 122. The lens 120 is configured to focus the fluorescence emission 110 on an inlet of the fiber optic cable 122. The fiber optic cable 122 is configured to guide or otherwise pass the focused light from the inlet to an outlet. The one or more optical components 108 may use different or less components than the illustrated components without departing from the scope of the disclosure. For example, the lens 120 may focus the light directly onto the detector 112 without including the fiber optic cable 122. The lens can include a quartz convex lens, or any other lens appropriate for the wavelengths being measured.

The detector 112 can detect an intensity of the fluorescence emission 110. Examples of detected intensities are described later within this disclosure. In some implementations, the detector 112 can include a monochromator 114 coupled to a photomultiplier 116. The monochromator 114 spatially disperses the fluorescence emission 110 into spectral components while the photomultiplier acts to amplify the detected fluorescence emission 110.

In some implementations, the apparatus 100 can include a microprocessor 124 and a computer-readable storage medium 126 that can store instructions executable by the microprocessor 124. Details on such processes are described later within the specification.

In some aspects of operation, the excitation light source 104 emits the light beam 106 towards the sample 102. After the beam 106 impacts the sample 102, a reflected light 128 is directed to a beam dump 130 while a fluorescent light 110 is emitted towards the detector 112. As the beam impacts the sample 102, either the sample 102 or the light source 104 can be moved, rotated, or adjusted to change the angle of incidence of the light beam 106 and the surface of the sample holder 102. The angle can be recorded along with an intensity of the emitted fluorescent light 110. All of the previously described components can be combined into a compact, portable unit that can be used in field operations.

Figure 2B:
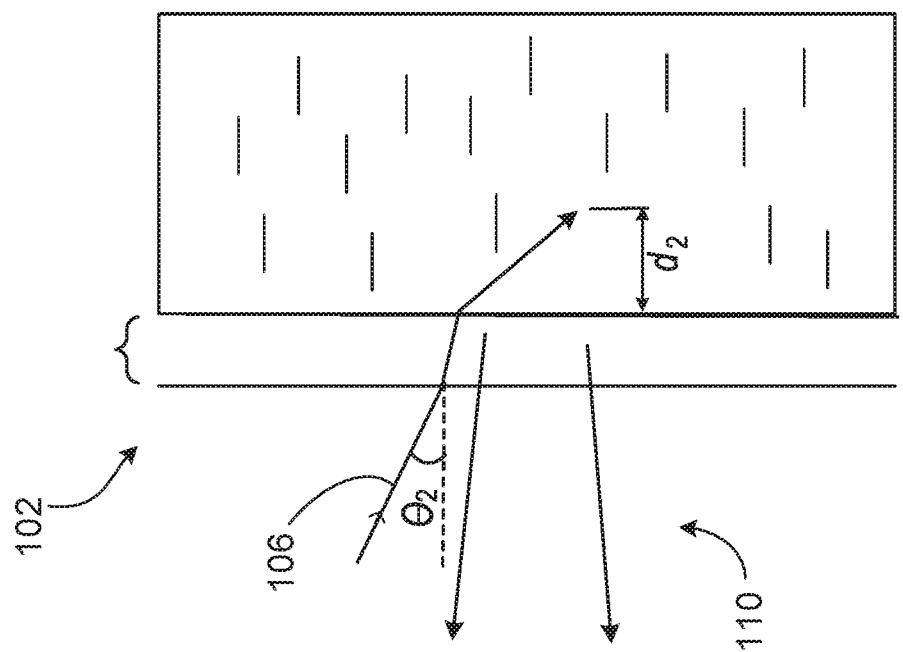
FIGS. 2A-2B are schematic diagrams showing a side cross sectional view of a sample holder containing a sample.
Figure 2A:
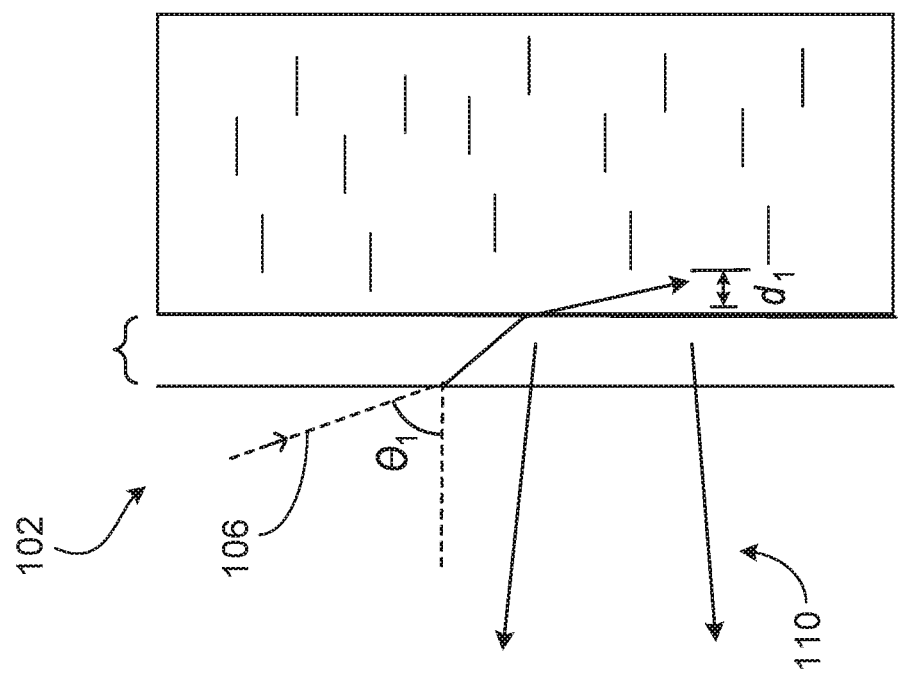

FIGS. 2A-2B illustrate detailed cross-sectional views of the example light beam 106 directed toward a surface of the example sample holder 102. The sample holder 102 can be a quartz cuvette, a glass sample container, or any other sample container with a flat surface that is transparent to the specified wavelengths of the light beam 106. A beam of light directed toward the surface of the sample holder 102 at a shallow angle, as shown in FIG. 2A, can experience a certain depth of penetration into the sample (d1). If the angle is steepened relative to the surface, as shown in FIG. 2B, then a greater depth of penetration (d2) can occur. Varying depths of penetration can result in varying degrees of intensity of the emitted fluorescence emission 110. By varying the angle of incidence and recording a change in fluorescent intensity with the detector 112, a plot can be created. Different fluids can produce different plots such that the different fluids can be identified. Details of such plots are discussed later within this disclosure. In order to vary the angle (and the depth of penetration), at least one of the sample or the light source can be moved (for example, rotated). For example, the incidence angle of the light beam 106 relative to the surface of the sample holder 102 can vary from 0°-80°.

Figure 3A:
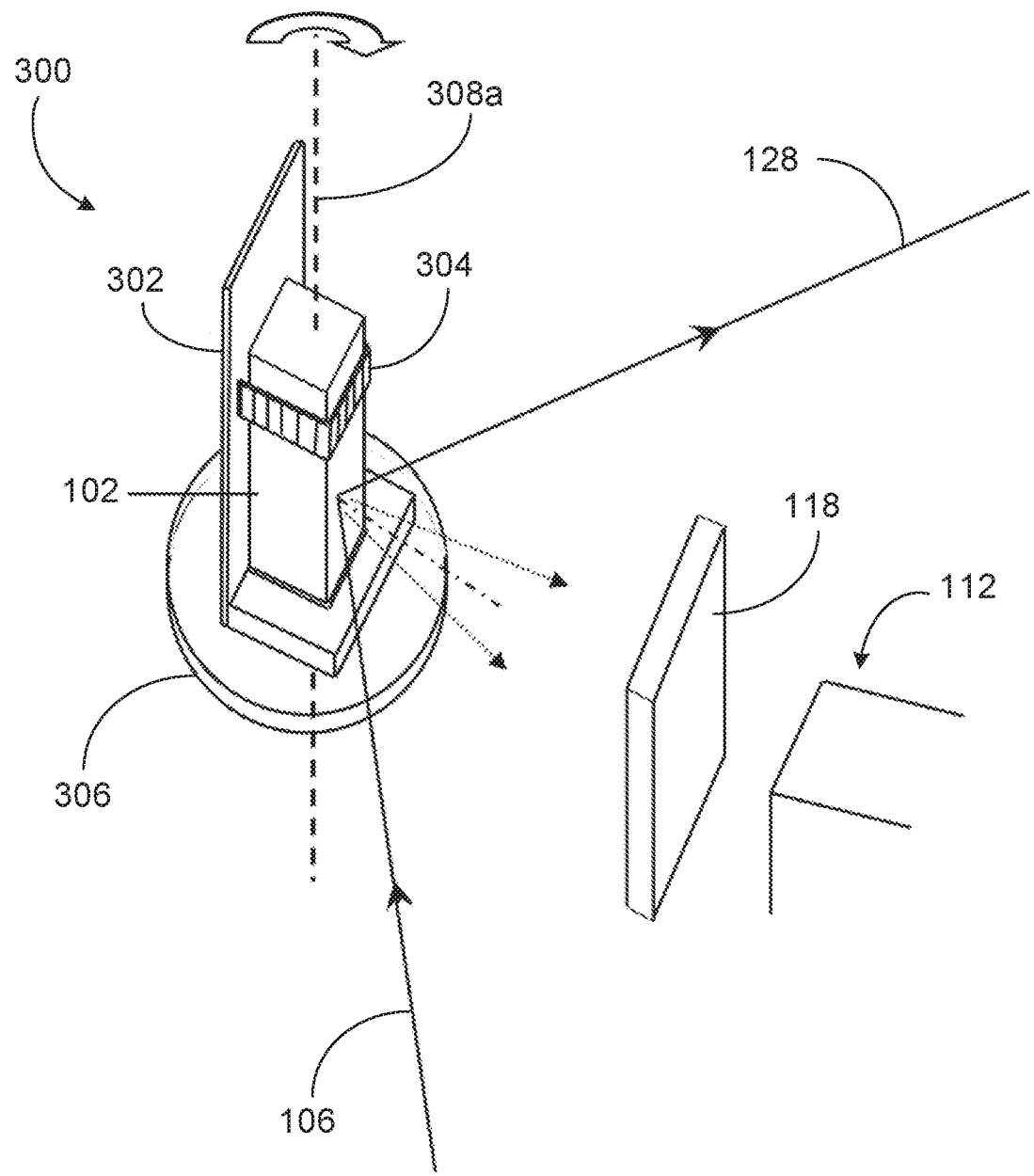
FIGS. 3A-3B are schematic diagrams showing perspective views of rotatable sample holder mounts.
Figure 3B:
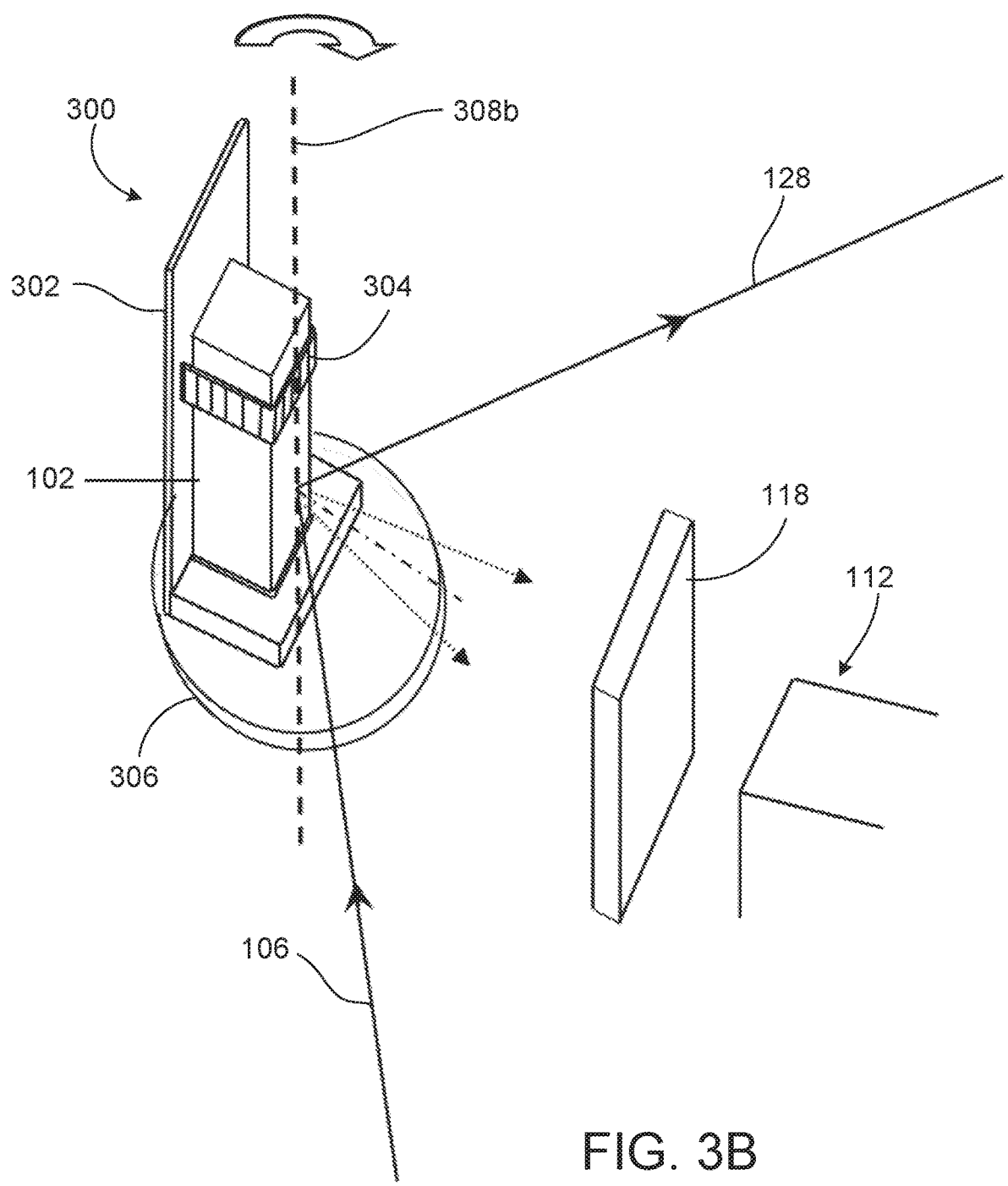
Figure 4B:
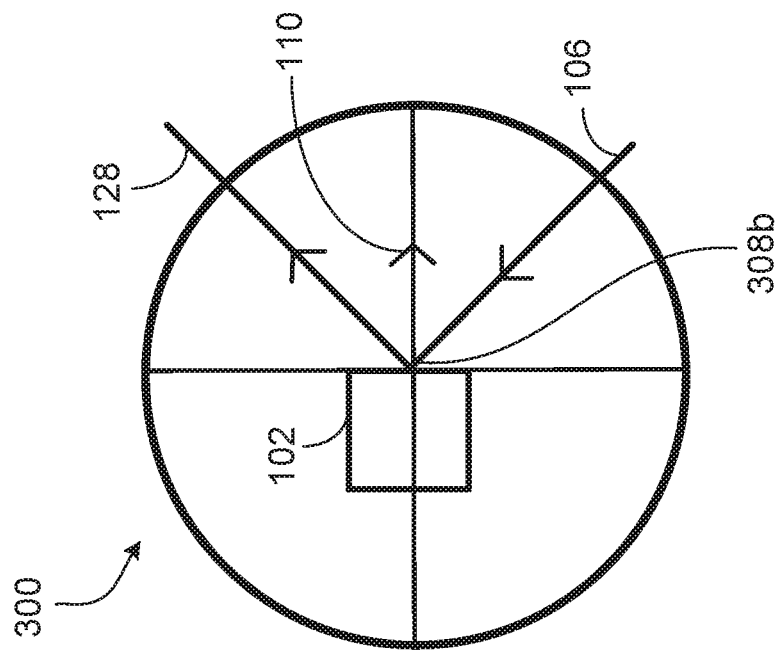
FIGS. 4A-4B are schematic diagrams showing top-down views of rotatable sample holder mounts.
Figure 4A:
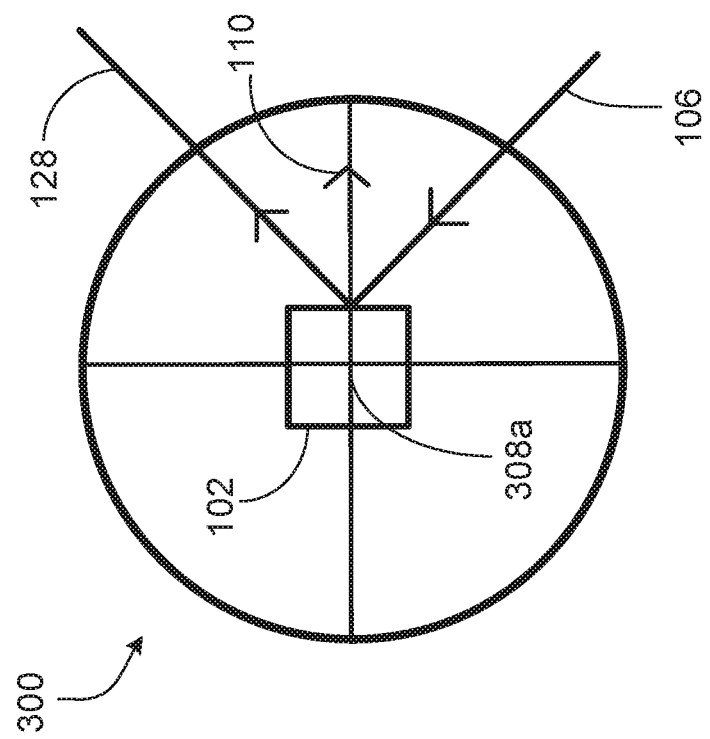

FIGS. 3A-3B are perspective detailed views of an example sample holder mount 300. In this example, the sample holder 102 is a rectangular shape and is supported by a vertical support 302. Sample holder 102 can be connected to the vertical support by a strap 304 or other types of attachments. In this example, the sample holder 102 is connected, by its base, to a rotation stage 306. As previously mentioned, to change the angle of incidence, the sample holder 102 can be moved, the light source 104 can be moved, or both can be moved. The illustrated example demonstrated one implementation of adjusting the angle of incidence by moving the sample holder 102. That is, the rotation stage 306 can be attached to a base of the sample holder 102 and is capable of rotating the surface of the sample holder 102 relative to the propagation axis of the excitation light. In illustrated implementations, the sample holder 102 can be rotated about a central vertical axis 308*a* that passes vertically through the center of the sample holder 102. In some implementations, the sample holder 102 can be rotated about a vertical axis 308*b* off set from the central axis of the sample holder 102. FIGS. 4A-4B are top-down views of a sample holder 102 positioned on a rotation stage 306. As illustrated by FIG. 4A, the axis of rotation 308*a* of the sample holder 102 can be positioned vertically through the center of the sample holder 102. As illustrated in FIG. 4A, the axis of rotation 308*b* of the sample holder 102 can be positioned vertically through the center of the surface of the sample holder 102.

Figure 5:
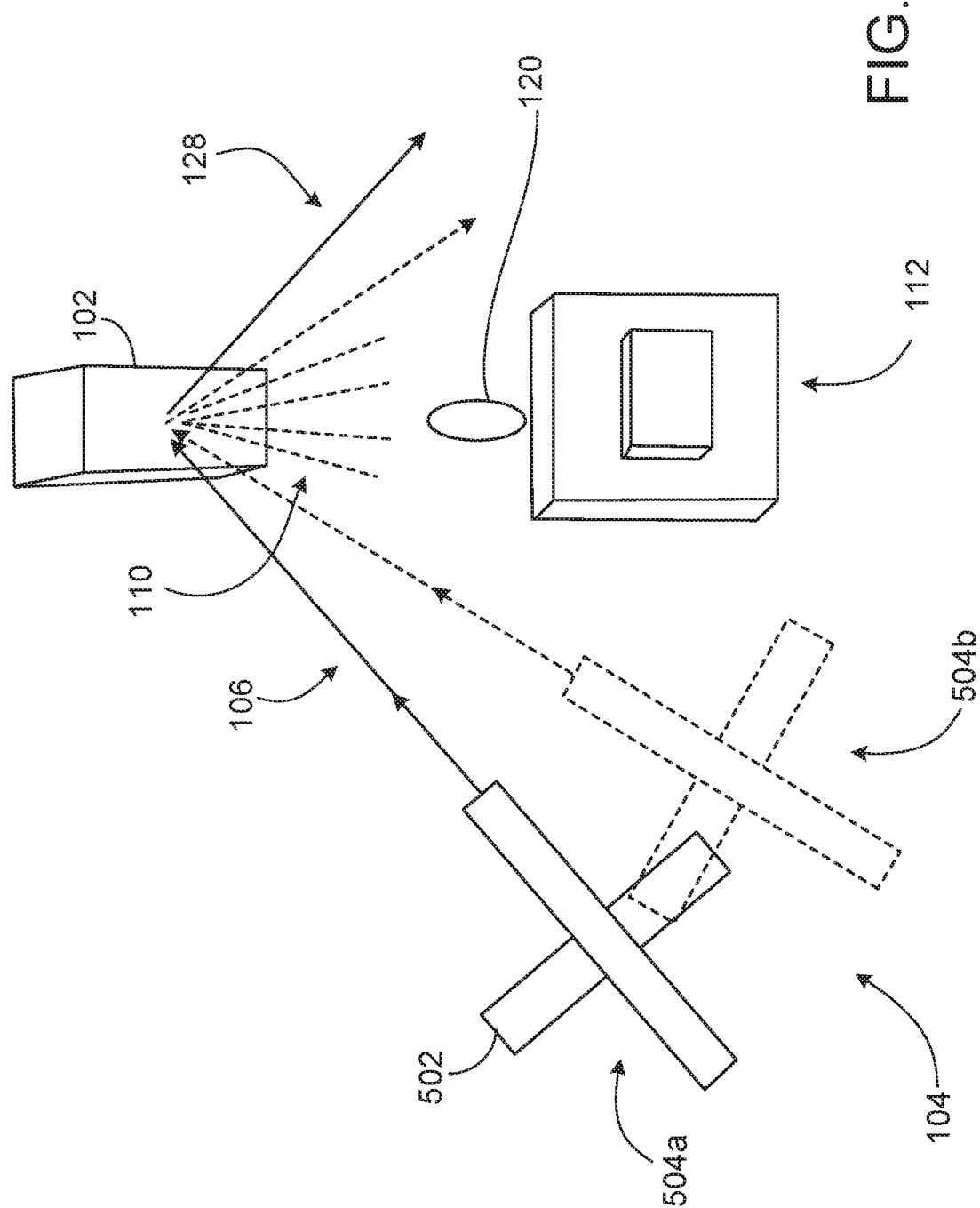
FIG. 5 is a schematic diagram showing a light source for the fluorescence-measurement apparatus.
Figure 6B:
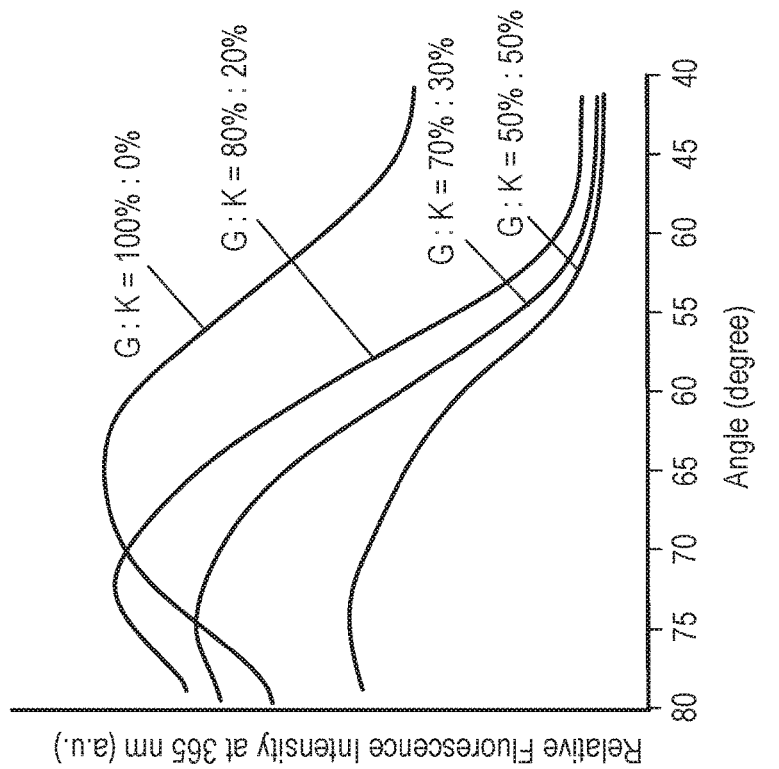
FIGS. 6A-6D are example plots of fluorescent intensities for different potential samples.
Figure 6A:
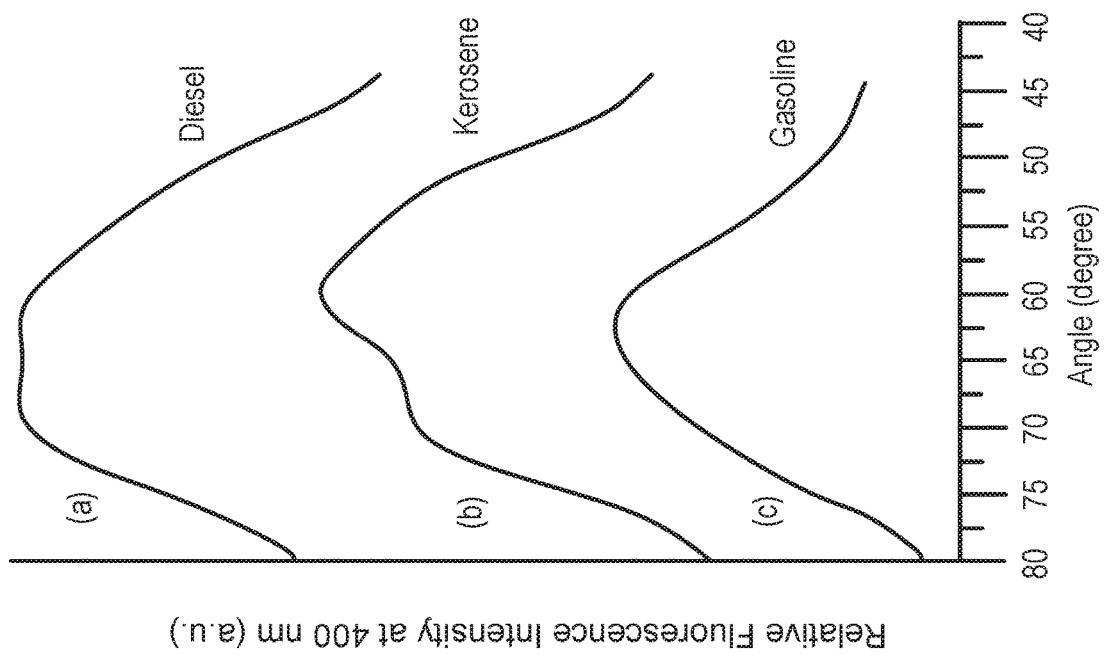
Figure 6C:
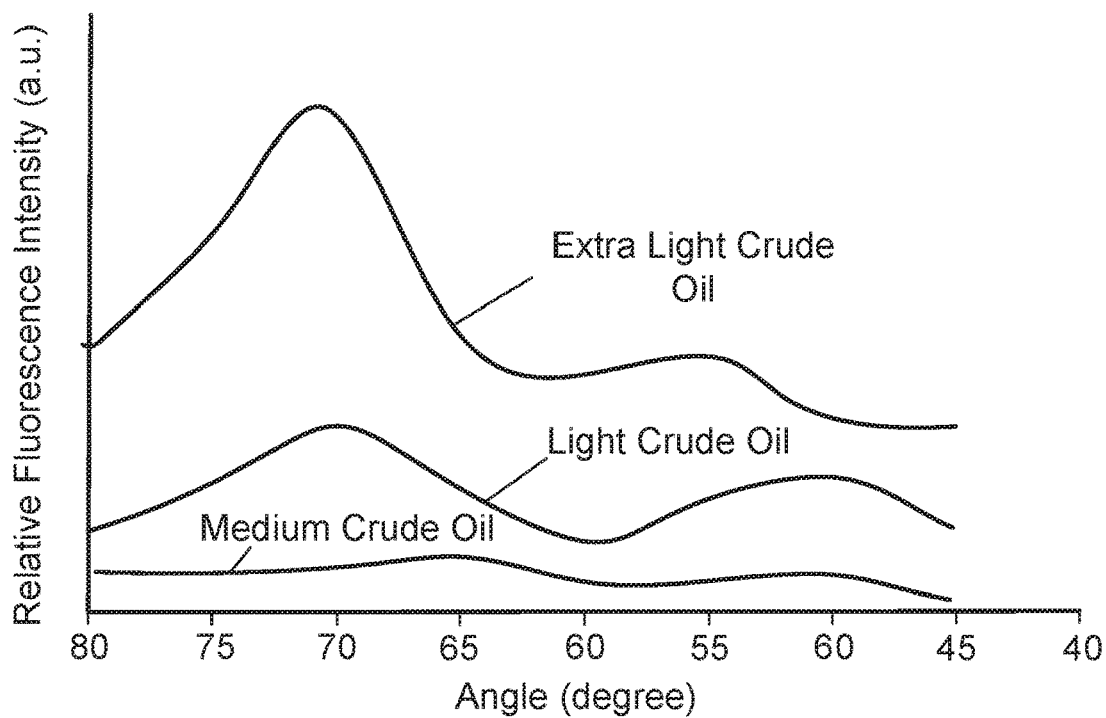
Figure 6D:
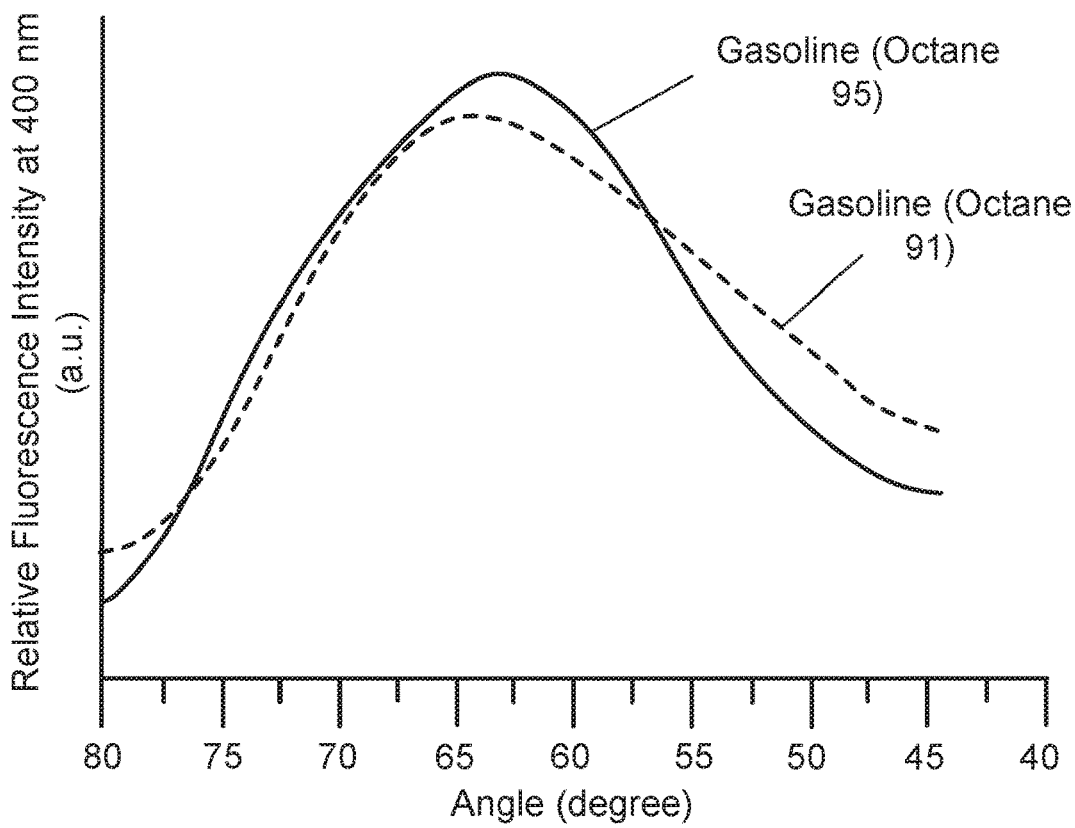

FIG. 5 is a schematic diagram showing an example implementation in which the light source 104 moves in order to adjust the angle of incidence rather than the sample holder 102. That is, a movable mount 502 can be attached to the light source 104. The movable mount 502 can change an incident angle of the excitation light source 104 relative to the surface of the sample holder 102. This is accomplished by moving the excitation light source 104 from a first position 504*a* to a second position 504*b*. In some implementations, the beam catcher 130 can move in conjunction with the light source 104 or the sample holder 102.

FIGS. 6A-6D are example plots that can be plotted based upon an intensity of the fluorescent emissions 110 emitted from a sample within the sample holder 102 in relation to the incidence angle. In some instances, the sample can include a hydrocarbon fluid. The testing apparatus can produce plots with either a clear or opaque sample. Once a plot is recorded, it can be compared to a library of known plots to determine the contents of the sample.

Figure 7:
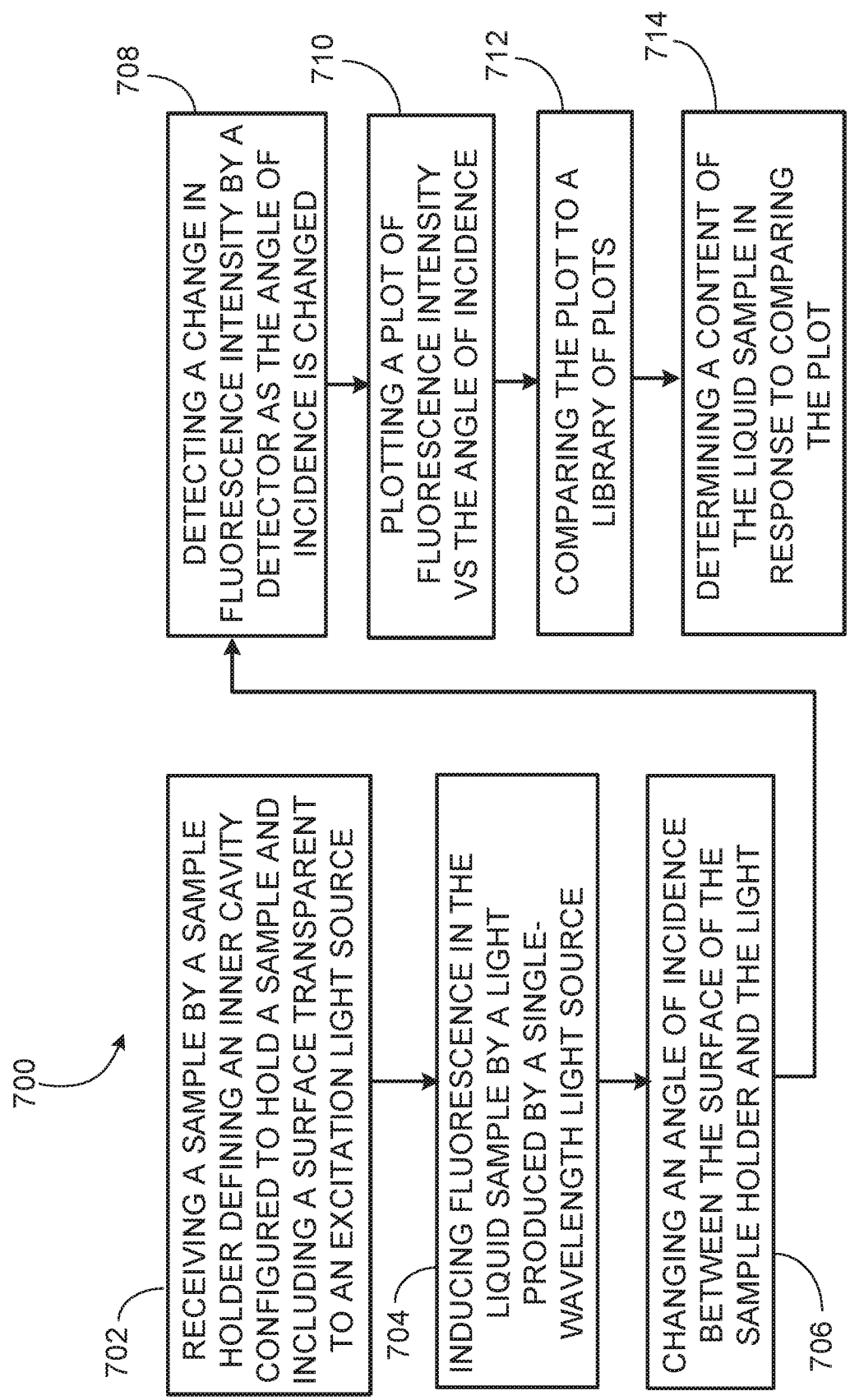
FIG. 7 is a flowchart of an example method for identifying a sample using fluorescent intensities.

FIG. 7 is a flowchart showing an example method 700 that can be used to determine a content of a sample. At 702, a sample is received by a sample holder that defines an inner cavity configured to hold a sample. The sample holder 102 includes a surface that is transparent to the excitation light source 104. In some implementations, the sample can be a fluid. At 704, fluorescence is induced in the fluid sample by a single-wavelength light beam 106 produced by the light source 104. At 706, an angle of incidence between the surface of the sample holder and the light is changed. The angle of incidence can be changed by adjusting an angle and position of the light source 104, an angle of the sample holder 102, or both. The change in the angle of incidence can vary between 0°-80°. At 708, a change in fluorescence intensity is detected by a detector 112 as the angle of incidence is changed. At 710, a plot of fluorescence intensity vs. the angle of incidence is plotted. At 712, the plot is compared to a library of plots. At 714, a content of the sample is determined in response to comparing the plot. In some implementations, aspects of the method 700 can be at least partially executed by the microprocessor 124.

Implementations of the subject matter and the operations described in this disclosure can be implemented in digital electronic circuitry, or in computer software, firmware, or hardware, including the structures disclosed in this disclosure and their structural equivalents, or in combinations of one or more of them. Implementations of the subject matter described in this disclosure can be implemented as one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, such as, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (such as, multiple CDs, disks, or other storage devices).

The operations described in this disclosure can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, such as, an FPGA (field programmable gate array) or an ASIC (application-specific integrated circuit). The apparatus can also include, in addition to hardware, code that creates an execution environment for the computer program in question, such as, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (such as, one or more scripts stored in a markup language document), in a single file dedicated to the program in question, or in multiple coordinated files (such as, files that store one or more modules, sub-programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, such as, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, such as, magnetic, magneto-optical disks, or optical disks. However, a computer need not have such devices. Moreover, a computer can be embedded in another device, such as, a mobile telephone, a personal digital assistant (PDA), a mobile audio or video player, a game console, a Global Positioning System (GPS) receiver, or a portable storage device (such as, a universal serial bus (USB) flash drive), to name just a few. Devices suitable for storing computer program instructions and data include all forms of non-volatile memory, media and memory devices, including by way of example semiconductor memory devices, such as, EPROM, EEPROM, and flash memory devices; magnetic disks, such as, internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this disclosure can be implemented on a computer having a display device, such as, a CRT (cathode ray tube) or LCD (fluid crystal display) monitor, for displaying information to the user and a keyboard and a pointing device, such as, a mouse or a trackball, by which the user can provide input to the computer. Other kinds of devices can be used to provide for interaction with a user as well; for example, feedback provided to the user can be any form of sensory feedback, such as, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While this disclosure contains many specific implementation details, these should not be construed as limitations on the scope of what may be claimed, but rather as descriptions of features specific to particular implementations of particular inventions. Certain features that are described in this disclosure in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed to achieve desirable results. Moreover, the separation of various system components in the implementations described above should not be understood as requiring such separation in all implementations, and it should be understood that the described components can generally be integrated together in a single product or packaged into multiple products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A fluorescence-measurement apparatus, comprising:
    a single-wavelength light source configured to generate an excitation light;
    a sample holder defining an inner cavity configured to hold a sample and including a surface transparent to the excitation light, the light source and the sample holder spatially arranged such that, during a sample test, a portion of the excitation light incident on the surface passes through the surface and is incident on the sample in the sample holder at a depth from the surface, wherein the sample is configured to emit fluorescence in response to the portion of the excitation light incident on the sample at the depth from the surface;
    one or more mounts attached to at least one of the light source or the sample holder and configured to actively change an incident angle of the excitation light incident on the surface during the sample test and responsively vary the depth from the surface at which the portion of the excitation light is incident on the sample, wherein the one or more mounts comprises a rotatable mount attached to a base of the sample holder and configured to rotate the surface of the sample holder in relation to the excitation light source;
    one or more optical components spatially arranged to receive a portion of the fluorescence emitted by the sample and passing through the surface and configured to guide the received to a detector; and
    the detector configured to detect an intensity of the fluorescence emission.

2. The fluorescence-measurement apparatus of claim 1, wherein an axis of rotation of the sample holder is positioned vertically through the center of the sample holder.

3. The fluorescence-measurement apparatus of claim 1, wherein an axis of rotation of the sample holder is positioned vertically through the center of the surface of the sample holder.

4. The fluorescence-measurement apparatus of claim 1, wherein the surface is tilted relative to a vertical axis in range from 0°-80°.

5. The fluorescence-measurement apparatus of claim 1, wherein the light source comprises a laser in an ultraviolet spectrum at a defined wavelength.

6. The fluorescence-measurement apparatus of claim 1, wherein the detector comprises a monochromator coupled to a photomultiplier.

7. The fluorescence-measurement apparatus of claim 1, further comprising a filter positioned between the surface and the detector and configured to pass a specified range of wavelengths and filter out wavelengths different from the specified range.

8. The fluorescence-measurement apparatus of claim 1, wherein the one or more optical components comprise:
    a lens positioned between the surface and the detector and configured to focus the fluorescence emission on an inlet of a fiber optic cable; and
    a fiber optic cable positioned between the lens and the detector and having the inlet configured to receive the focused fluorescence emission and an outlet positioned to direct the focused fluorescence emission to the detector.

9. The fluorescence-measurement apparatus of claim 1, wherein the sample comprises a hydrocarbon fluid.

* * * * *